US009487812B2

(12) United States Patent
Neeves et al.

(10) Patent No.: US 9,487,812 B2
(45) Date of Patent: Nov. 8, 2016

(54) OPTICAL ALIGNMENT DEFORMATION SPECTROSCOPY

(71) Applicant: Colorado School of Mines, Golden, CO (US)

(72) Inventors: Keith B. Neeves, Denver, CO (US); David W. M. Marr, Golden, CO (US); Kevin B. Roth, Golden, CO (US); Charles D. Eggleton, Baltimore, MD (US)

(73) Assignee: Colorado School of Mines, Golden, CO (US)

( * ) Notice: Subject to any disclaimer, the term of this patent is extended or adjusted under 35 U.S.C. 154(b) by 98 days.

(21) Appl. No.: 13/770,875

(22) Filed: Feb. 19, 2013

(65) Prior Publication Data

US 2013/0230879 A1 Sep. 5, 2013

Related U.S. Application Data

(60) Provisional application No. 61/600,482, filed on Feb. 17, 2012.

(51) Int. Cl.
*B01L 99/00* (2010.01)
*G01N 15/14* (2006.01)
*C12Q 1/02* (2006.01)
*B01L 3/00* (2006.01)

(52) U.S. Cl.
CPC ........... *C12Q 1/02* (2013.01); *B01L 3/502761* (2013.01); *G01N 15/1484* (2013.01); *B01L 2200/0668* (2013.01); *B01L 2400/0463* (2013.01); *B01L 2400/0487* (2013.01); *G01N 2015/1495* (2013.01)

(58) Field of Classification Search
CPC ............................................. G01N 2015/1495
See application file for complete search history.

(56) References Cited

U.S. PATENT DOCUMENTS

| 4,190,535 | A | 2/1980 | Luderer |
| 5,002,647 | A | 3/1991 | Tanabe et al. |
| 5,021,224 | A | 6/1991 | Nakajima |
| 5,098,850 | A | 3/1992 | Nishida et al. |
| 5,148,511 | A | 9/1992 | Savu et al. |

(Continued)

FOREIGN PATENT DOCUMENTS

| DE | 19712309 | 5/1998 |
| EP | 1221342 | 7/2002 |

(Continued)

OTHER PUBLICATIONS

Davies et al. "Optically controlled collisions of biological objects" (1998).*

(Continued)

*Primary Examiner* — Paul Hyun
(74) *Attorney, Agent, or Firm* — Sheridan Ross P.C.

(57) ABSTRACT

A microfluidic system, device, and method are disclosed. The microfluidic system may include a first microfluidic channel and a second microfluidic channel, each of which are carrying one or more objects. There is an intersection between the first and second microfluidic channels where one or more objects from the first microfluidic channel impact one or more objects from the second microfluidic channel under hydrodynamic forces. The impact causes the objects to deform and the deformation of objects can be analyzed to determine properties of the object.

18 Claims, 8 Drawing Sheets

(56) References Cited

U.S. PATENT DOCUMENTS

| | | |
|---|---|---|
| 5,176,786 A | 1/1993 | Debe |
| 5,187,089 A | 2/1993 | Scott et al. |
| 5,304,487 A | 4/1994 | Wilding et al. |
| 5,427,663 A | 6/1995 | Austin |
| 5,512,745 A | 4/1996 | Finer et al. |
| 5,541,072 A | 7/1996 | Wang et al. |
| 5,622,831 A | 4/1997 | Liberti et al. |
| 5,639,669 A | 6/1997 | Ledley |
| 5,707,799 A | 1/1998 | Hansmann et al. |
| 5,715,946 A | 2/1998 | Reichenbach |
| 5,750,339 A | 5/1998 | Smith |
| 5,753,038 A | 5/1998 | Vichr et al. |
| 5,770,029 A | 6/1998 | Nelson et al. |
| 5,837,115 A | 11/1998 | Austin |
| 5,855,753 A | 1/1999 | Trau et al. |
| 5,858,188 A | 1/1999 | Soane et al. |
| 5,866,345 A | 2/1999 | Wilding et al. |
| 5,928,880 A | 7/1999 | Wilding et al. |
| 5,952,173 A | 9/1999 | Hansmann et al. |
| 6,007,690 A | 12/1999 | Nelson |
| 6,017,390 A | 1/2000 | Charych et al. |
| 6,054,034 A | 4/2000 | Soane et al. |
| 6,055,106 A | 4/2000 | Grier et al. |
| 6,067,859 A | 5/2000 | Kas et al. |
| 6,074,827 A | 6/2000 | Nelson |
| 6,128,006 A | 10/2000 | Rosenberg et al. |
| 6,156,270 A | 12/2000 | Buechler |
| 6,187,089 B1 | 2/2001 | Phillips et al. |
| 6,197,523 B1 | 3/2001 | Rimm et al. |
| 6,221,671 B1 | 4/2001 | Groner et al. |
| 6,241,894 B1 | 6/2001 | Briggs et al. |
| 6,251,691 B1 | 6/2001 | Seul |
| 6,256,093 B1 | 7/2001 | Ravid et al. |
| 6,256,096 B1 | 7/2001 | Johnson |
| 6,265,229 B1 | 7/2001 | Fodstad et al. |
| 6,315,940 B1 | 11/2001 | Nisch et al. |
| 6,344,326 B1 | 2/2002 | Nelson |
| 6,361,958 B1 | 3/2002 | Shieh |
| 6,368,871 B1 | 4/2002 | Christel et al. |
| 6,387,290 B1 | 5/2002 | Brody et al. |
| 6,406,903 B2 | 6/2002 | Bray et al. |
| 6,432,630 B1 | 8/2002 | Blankenstein |
| 6,454,938 B2 | 9/2002 | Moon et al. |
| 6,465,225 B1 | 10/2002 | Fuhr et al. |
| 6,468,346 B2 | 10/2002 | Arnowitz et al. |
| 6,533,903 B2 | 3/2003 | Hayward et al. |
| 6,540,895 B1 | 4/2003 | Spence et al. |
| 6,565,225 B2 | 5/2003 | Mabuchi et al. |
| 6,613,525 B2 | 9/2003 | Nelson et al. |
| 6,632,619 B1 | 10/2003 | Harrison et al. |
| 6,635,163 B1 | 10/2003 | Han et al. |
| 6,664,104 B2 | 12/2003 | Pourahmadi et al. |
| 6,685,841 B2 | 2/2004 | Lopez et al. |
| 6,744,038 B2 | 6/2004 | Wang et al. |
| 6,746,503 B1 | 6/2004 | Benett et al. |
| 6,762,059 B2 | 7/2004 | Chan et al. |
| 6,783,647 B2 | 8/2004 | Culbertson et al. |
| 6,784,420 B2 | 8/2004 | Wang et al. |
| 6,797,057 B1 | 9/2004 | Amos et al. |
| 6,802,489 B2 | 10/2004 | Marr et al. |
| 6,815,664 B2 | 11/2004 | Wang et al. |
| 6,830,936 B2 | 12/2004 | Anderson et al. |
| 6,833,542 B2 | 12/2004 | Wang et al. |
| 6,878,271 B2 | 4/2005 | Gilbert et al. |
| 6,881,315 B2 | 4/2005 | Iida et al. |
| 6,893,502 B2 | 5/2005 | Papadimitrakopoulos et al. |
| 6,893,881 B1 | 5/2005 | Fodstad et al. |
| 6,913,697 B2 | 7/2005 | Lopez et al. |
| 6,958,245 B2 | 10/2005 | Seul et al. |
| 6,991,939 B2 | 1/2006 | Walt et al. |
| 7,068,874 B2 | 6/2006 | Wang et al. |
| 7,088,455 B1 | 8/2006 | Kirkpatrick et al. |
| 7,150,812 B2 | 12/2006 | Huang et al. |
| 7,155,082 B2 | 12/2006 | Oakey et al. |
| 7,202,045 B2 | 4/2007 | Hanash et al. |
| 7,205,157 B2 | 4/2007 | Jurgensen et al. |
| 7,214,298 B2 | 5/2007 | Spence et al. |
| 7,214,348 B2 | 5/2007 | Desmond et al. |
| 7,241,988 B2 | 7/2007 | Gruber et al. |
| 7,276,170 B2 | 10/2007 | Oakey et al. |
| 7,294,503 B2 | 11/2007 | Quake et al. |
| 7,312,085 B2 | 12/2007 | Chou et al. |
| 7,318,902 B2 | 1/2008 | Oakey et al. |
| 7,435,568 B2 | 10/2008 | Kas et al. |
| 7,442,339 B2 | 10/2008 | Sundararajan et al. |
| 7,460,240 B2 | 12/2008 | Akcakir |
| 7,472,794 B2 | 1/2009 | Oakey et al. |
| 7,638,339 B2 | 12/2009 | Sundararajan et al. |
| 7,651,838 B2 | 1/2010 | Paterlini-Brechot |
| 7,713,705 B2 | 5/2010 | Buechler et al. |
| 7,745,788 B2 | 6/2010 | Appleyard et al. |
| 8,119,976 B2 | 2/2012 | Squier |
| 2002/0062783 A1 | 5/2002 | Bray |
| 2002/0108859 A1 | 8/2002 | Wang et al. |
| 2002/0113204 A1 | 8/2002 | Wang et al. |
| 2002/0115163 A1 | 8/2002 | Wang et al. |
| 2002/0123112 A1 | 9/2002 | Wang et al. |
| 2002/0172987 A1 | 11/2002 | Terstappen et al. |
| 2003/0024470 A1 | 2/2003 | Myerson |
| 2003/0072682 A1 | 4/2003 | Kikinis |
| 2003/0124516 A1 | 7/2003 | Chung et al. |
| 2005/0175478 A1 | 8/2005 | Marr et al. |
| 2006/0060767 A1 | 3/2006 | Wang et al. |
| 2006/0142632 A1 | 6/2006 | Meretei |
| 2006/0171846 A1 | 8/2006 | Marr |
| 2007/0125941 A1 | 6/2007 | Lee et al. |
| 2008/0093306 A1 | 4/2008 | Oakey et al. |
| 2009/0062828 A1 | 3/2009 | Marr |
| 2009/0110010 A1 | 4/2009 | Squier |
| 2009/0188795 A1 | 7/2009 | Oakey et al. |
| 2013/0183660 A1* | 7/2013 | Yu et al. ............... 435/5 |

FOREIGN PATENT DOCUMENTS

| | | |
|---|---|---|
| EP | 1412729 | 1/2003 |
| EP | 1438398 | 5/2003 |
| EP | 1338894 | 8/2003 |
| EP | 1485713 | 9/2003 |
| EP | 1499706 | 10/2003 |
| EP | 1539350 | 1/2004 |
| EP | 1529211 | 2/2004 |
| EP | 1542802 | 3/2004 |
| EP | 1418003 | 5/2004 |
| EP | 1462800 | 9/2004 |
| EP | 919812 | 10/2004 |
| WO | WO 94/29707 | 12/1994 |
| WO | WO 98/10267 | 3/1998 |
| WO | WO 99/44064 | 9/1999 |
| WO | WO 00/00816 | 1/2000 |
| WO | WO 02/12896 | 2/2002 |
| WO | WO 02/28523 | 4/2002 |
| WO | WO 02/30562 | 4/2002 |
| WO | WO 02/44689 | 6/2002 |
| WO | WO 03/031938 | 4/2003 |
| WO | WO 03/066191 | 8/2003 |
| WO | WO 2004/029221 | 4/2004 |
| WO | WO 2004/037374 | 5/2004 |
| WO | WO 2004/056978 | 7/2004 |

OTHER PUBLICATIONS

Ashkin et al. "Optical Trapping and Manipulation of Viruses and Bacteria," Science, Mar. 1987, vol. 235, No. 4795, pp. 1517-1520.

Baldessari et al. "Two touching spherical drops in uniaxial extensional flow: Analytic solution to the creeping flow problem," Journal of Colloid and Interface Science, Sep. 2005, vol. 289, No. 1, pp. 262-270.

Duffy et al. "Rapid Prototyping of Microfluidic Systems in Poly(dimethylsiloxane)" Analytical Chemistry, Dec. 1998, vol. 70, No. 23, pp. 4974-4984.

Guck et al. "The Optical Stretcher: A Novel Laser Tool to Micromanipulate Cells," Biophysical Journal, Aug. 2001, vol. 81, pp. 767-784.

(56) References Cited

OTHER PUBLICATIONS

Sraj et al. "Cell deformation cytometry using diode-bar optical stretchers," Journal of Biomedical Optics, Jul./Aug. 2010, vol. 15, No. 4, 7 pages.

U.S. Appl. No. 14/307,269, filed Jun. 17, 2014, Sawetski et al.

Applegate et al., "Microfluidic sorting system based on optical waveguide integration and diode laser bar trapping", Lab on a Chip, Jan. 20, 2006, vol. 6, pp. 422-426, The Royal Society of Chemistry.

Applegate et al., "Optical trapping, manipulation, and sorting of cells and colloids in microfluidic systems with diode laser bars", Colorado School of Mines, 2002, pp. 1-9.

Archer et al. "Cell Reactions to Dielectrophoretic Manipulation." Biochemical and Biophysical Research Communications. 1999;257:687-98.

Ashcroft et al., "Solid State Physics." Orlando, FL: Saunders College Publishing; 1976.

Author Unknown, "MicCell: Frequently Asked Questions", available at www.gesim.de, 2007, 4 pages.

Author Unknown, "The Optical Stretcher", available at http://www.uni/leipzig.de/~pwm/kas/os/os.html, cite updated on Nov. 23, 2005, 2 pages.

Bauer, "Advances in cell separation: recent developments in counterflow centrifugal elutriation and continuous flow cell separation." Journal of Chromatography.1999;722:55-69.

Becker et al. "Fabrication of Microstructures With High Aspect Ratios and Great Structural heights by Synchrotron Radiation Lithography, Galvanoforming, and Plastic Moulding (LIGA Process)." Microelectronic Engineering. 1986;4:35-56.

Becker et al. "Planar quartz chips with submicron channels for two-dimensional capillary electrophoresis applications." J. Micromech Microeng.1998;9:24-28.

Beebe et al., "Functional Hydrogel Structures for Autonomous Flow Control Inside Microfluidic Channels", Nature, Apr. 6, 2000, pp. 588-590, 404, Nature Publishing Group (USA), a division of Macmillan Publishers Ltd., United Kingdom.

Benincasa et al. "Cell Sorting by One Gravity SPLITT Fractionation." Analytical Chemistry. 2005; 77(16):5294-5301.

Berg, "Random Walks in Biology." Princeton University Press. Princeton, NJ; 1993.

Brown et al. "Optical Waveguides Via Viscosity-Mismatched Microfluidic Flows." Department of Chemical Engineering, Colorado School of Mines. Applied Physics Letters 88, 134109 (2006).

Chan, et al., "DNA Mapping Using Microfluidic Stretching and Single-Molecule Detection of Flourescent Site-Specific Tags", Genome Research, 2004, vol. 14, pp. 1137-1146, Cold Spring Harbor Laboratory Press.

Chiu et al., "Patterned Deposition of Cells and Proteins Onto Surfaces by Using Three-Dimensional Microfluidic Systems", Proceedings of the National Academy of Sciences of the United States of America, Mar. 14, 2000, pp. 2408-2413, 97-#6, National Academy of Sciences, USA.

Chou et al., "A Microfabricated Device for Sizing and Sorting DNA Molecules", Proceedings of the National Academy of Sciences of the United States of America, Jan. 5, 1999, pp. 11-13, 96-#1, National Academy of Sciences, USA.

Chou et al., "Sorting by diffusion: An asymmetric obstacle course for continuous molecular separation." PNAS. 1999; 96(24):13762-13765.

De Kretser et al., "The Separation of Cell Populations using Monoclonal Antibodies attached to Sepharose." Tissue Antigens. 1980;16:317-325.

Delamarche et al., "Microfluidic Networks for Chemical Patterning of Substrates: Design and Application to Bioassays", Journal of the American Chemical Society, Jan. 9, 1998, pp. 500-508, 120, American Chemical Society, USA.

Delamarche et al., "Patterned Delivery of Immunoglobulins to Surfaces Using Microfluidic Networks", Science, May 2, 1997, pp. 779-781, 276, American Association for the Advancement of Science, USA.

Deshmukh et al., "Continuous Micromixer With Pulsatile Micropumps. Solid-State Sensor and Actuator Workshop." Hilton Head Island, South Carolina; Jun. 4-8, 2000:73-76.

Desprat, et al., "Creep Function of a Single Living Cell", Biophysical Journal, Mar. 2005, vol. 88, pp. 2224-2233, Biophysical Society.

Eigen et al., "Sorting Single Molecules: Application to Diagnostics and Evolutionary Biotechnology", Proceedings of the National Academy of Sciences of the United States of America, Jun. 1994, pp. 5740-5747, 91, National Academy of Sciences, USA.

Evans et al., "The Bubble Spring and Channel (BSAC) Valve: An Actuated, Bi-Stable Mechanical Valve for In-Plane Fluid Control. Transducers '99." Sendai, Japan; Jun. 7-10, 1999.

Eyal et al., "Velocity-independent microfluidic flow cytometry", Electrophoresis, Aug. 2002;23(16):2653-7 (abstract only).

Farooqui et al. "Microfabrication of Submicron Nozzles in Silicon Nitride." Journal of Microelectromechanical Systems. 1992; 1(2):86-88.

Fiedler et al., "Dielectrophoretic Sorting of Particles and Cells in a Microsystem", Analytical Chemistry, May 1, 1998, pp. 1909-1915, 70-#9, American Chemical Society, USA.

Freemantle, "Downsizing Chemistry", Chemical & Engineering News, Feb. 22, 1999, pp. 27-39, 77-#8, American Chemical Society.

Fu et al., "A Microfabricated Flourescence-Activated Cell Sorter", Nature Biotechnology, Nov. 1999, pp. 1109-1111, 17, Nature America Inc., USA.

Fu et al., "An integrated miscrofabricated cell sorter." Analytical Chemistry. 2002;74(11):2451-2457.

Fuhr et al., "Biological Application of Microstructures", Topics in Current Chemistry, 1997, pp. 83-116, 194, Springer-Verlag, Germany.

Gambin et al. "Microfabricated Rubber Microscope Using Soft Solid Immersion Lenses." Department of Applied Physics, California Institute of Technology. Applied Physics Letters 88, 174102 (2006).

Gast, et al., "The development of integrated microfluidic systems at GeSiM", Lab on a Chip, 2003, vol. 3, pp. 6N-1 ON, The Royal Society of Chemistry.

Gast, et al., "The microscopy cell (MicCell), a versatile modular flowthrough system for cell biology, biomaterial research, and nanotechnology", Microfluid Nanofluid (2006), published on-line Jul. 27, 2005, vol. 2, pp. 21-36, Springer-Verlag.

Giddings, "Chemistry 'Eddy' Diffusion in Chromatography." Nature. 1959;184:357-358.

Giddings, "Field-Flow Fractionation: Analysis of Macromolecular, Colloidal, and Particulate Materials." Science. 1993;260:1456-1465.

Giddings, "Unified Separation Science." John Wiley & Sons, Inc. 1991; Cover Page & Table of Contents only.

Gu, et al., "A single beam near-field laser trap for optical stretching, folding and rotation of erythrocytes", Optics Express, Feb. 5, 2007, vol. 15, No. 3., pp. 1369-1375, Optical Society of America.

Guck, et al., "The Optical Stretcher: A Novel Laser Tool to Micromanipulate Cells", Biophysical Journal, Aug. 2001, vol. 81, pp. 767-784, Biophysical Society.

Han et al., "Separation of Long DNA Molecules in a Microfabricated Entropic Trap Array." Science. 2000;288: 1026-1029.

Huang et al., "A DNA prism for high-speed continuous fractionation of large DNA molecules." Nature Biotechnology. 2002;20:1048-1051.

Huang et al., "Role of Molecular Size in Ratchet Fractionation." 2002; 89(17):178301-1-178301-4.

Huang et al., "Electric Manipulation of Bioparticles and Macromoledules on Microfabricated Electrodes", Analytical Chemistry, Apr. 1, 2001, pp. 1549-1559, 73-#7, American Chemical Society, USA.

Huh et al., "Gravity-driven microhydrodynamics-based cell sorter (microHYCS) for rapid, inexpensive, and efficient cell separation and size-profiling." 2nd Annual International IEEE-EMBS Special Topic Conference on Microtechnology in Medicine and Biology. Madison, Wisconsin USA; May 2-4, 2002:466-469.

(56) References Cited

OTHER PUBLICATIONS

Jeon et al., "Generation of Solution and Surface Gradients using Microfluidic Systems", Langmuir, 2000, pp. 8311-8316, 16-#22, American Chemical Society, USA.

Kamholz et al., "Quantitative Analysis of Molecular Interaction in a Microfluidic Channel: the T-Sensor", Analytical Chemistry, Dec. 1, 1999, pp. 5340-5347, 71-#23, American Chemical Society, USA.

Kenis et al., "Microfabrication Inside Capillaries Using Multiphase Laminar Flow Patterning", Science, Jul. 2, 1999, pp. 83-85, 285, American Association for the Advancement of Science, USA.

Kim et al. Polymer microstructures formed by moulding in capillaries. Nature. 1995;376:581-584.

Kim, et al., "Stretching and immobilization of DNA for studies of protein—DNA interactions at the single-molecule level", Nano Review, Apr. 18, 2007, Nanoscale Res Letter vol. 2, pp. 185-201, Springer.

Kumar et al. Cell Separation: A Review. Pathology. 1984;16:53-62.

Lang, et al., "Resource Letter: LBOT-1: Letter based optical tweezers", Am J Phys., Mar. 2003, vol. 71(3), pp. 201-215, National Institute of Health.

Li et al, "Transport, Manipulation, and Reaction of Biological Cells On-Chip Using Electrokinetic Effects", Analytical Chemistry, Apr. 15, 1997, pp. 1564-1568, 69-#8, American Chemical Society, USA.

Lim, et al., "Large deformation of living cells using laser traps", Acta Materialia, Apr. 19, 2004, vol. 52, Issue 7, pp. 1837-1845, Elsevier Science Ltd., (Only abstract and figures/tables provided, 6 pages).

Lincoln et al., "High-Throughput Rheological Measurements with an Optical Stretcher", Methods in Cell Biology, vol. 83, 2007, pp. 397-423 (abstract only).

Lincoln, et al., "Deformability-Based Flow Cytometry", Wiley InterScience, May 17, 2004, Cytometry Part A 59A, pp. 203-209, Wiley-Liss, Inc.

Lu, et al., "Viscoelastic properties of individual glial cells and neurons in the CNS", PNAS, Nov. 21, 2006, vol. 103, No. 47, pp. 17759-17764, The National Academy of Sciences of the USA.

Lumsdon et al. "Two-Dimensional Crystallization of Microspheres by a Coplanar AC Electric Field," 2004, Langmuir, vol. 20, pp. 2108-2116.

Martin et al., "Feeling with light for cancer", 2006, Progress in biomedical optics and imaging, vol. 7 (abstract only).

McClain et al., "Flow Cytometry of *Escherichia coli* on Microfluidic Devices", Anal. Chem., 73 (21), 5334-5338, 2001 (abstract only).

Mehrishi et al. "Electrophoresis of cells and the biological relevance of surface charge." Electrophoresis. 2002;23:1984-1994.

MicCell™ Parts List, GeSiM, www.gesim.de, 2007, 2 pages.

MicCell™ Special Designs (Selection), GeSiM, www.gesim.de, date unknown, 2 pages.

Moore et al. Lymphocyte fractionation using immunomagnetic colloid and a dipole magnet flow cell sorter. J Biochem Biophys Methods. 1998;37:11-33.

Oakey et al., "Laminar Flow-Based Separations at the Microscale", Biotechnology Progress, Sep. 24, 2002, pp. 1439-1442, 18-#6, American Chemical Society and the American Institute of Chemical Engineers, USA.

Olson et al., "An In Situ Flow Cytometer for the Optical Analysis of Individual Particles in Seawater", found at http://www.whoi.edu/science/B/Olsonlab/insitu2001.htm, publication date unknown.

Pamme et al., "Counting and sizing of particles and particle agglomerates in a microfluidic device using laser light scattering: application to a particle-enhanced immunoassay", Lap Chip, Mar. 2003, 187-192.

Product literature for GEM, a systme for blood testing: "GEM PCL Step by Step Guide" and "GEM Premier 3000", publication date unknown.

Raymond et al. "Continuous Separation of High Molecular Weight Compounds using a Microliter Volume Free-Flow Electrophoresis Microstructure." 1996;68:2515-2522.

Reed et al., "High throughput cell nanomechanics with mechanical imaging interferometry", 2008 Nanotechnology 19, 235101 (8 pages) (abstract only).

Sawetzki et al., "Viscoelasticity as a Biomarker for High-Throughput Flow Cytometry," 2013, Biophyiscal Journal, vol. 105(10), pp. 2281-2288.

Sery et al.,"Compact laser tweezers," 2007, Proc. SPIE 6609, 15th Czech-Polish-Slovak Conference on Wave and Quantum Aspects of Contemporary Optics, 66090N, 2 pages (abstract only).

Singh, et al., "A Miniaturized Wide-Angle 2D Cytometer", Wiley InterScience, Feb. 23, 2006, Cytometry Part A 69A, pp. 307-315, International Society for Analytical Cytology.

Takayama et al. "Patterning Cells and Their Environments Using Multiple Laminar Fluid Flows in Capillary Netwoorks", Proceedings of the National Academy of Sciences of the United States of America, May 11, 1999, pp. 5545-5548, 96-#10, national Academy of Sciences, USA.

Takayama et al. "Subcellular Position of Small Molecules", Nature, Jun. 28, 2001, p. 1016, 411, Nature Publishing Group (USA), a division of Macmillan Publishers Ltd., United Kingdom.

Terray et al., "Microfluidic Control Using Colloidal Devices", Science vol. 296, Jun. 7, 2002, pp. 1841-1844.

Tong et al. Low Temperature Wafer Direct Bonding. Journal of Microelectromechanical Systems. 1994;3:29-35.

Turner et al. Confinement-Induced Entropic Recoil of Single DNA Molecules in a Nanofluidic Structure. Physical Review Letters. 2002;88:128103.1-128103.4.

Vezenov et al. "Integrated Fluorescent Light Source for Optofluidic Applications." Department of Chemistry and Chemical Biology, Harvard University. Applied Physics Letters 86, 041104 (2005).

Visscher, et al., "Single Beam Optical Trapping Integrated in a Confocal Microscope for Biological Applications", Cytometry, Apr. 10, 1991, vol. 12, pp. 485-491, Wiley-Liss, Inc.

Voldman et al. Holding Forces of Single-Particle Dielectrophoretic Traps. Biophysical Journal.2001;80:531-541.

Volkmuth et al. DNA electrophoresis in microlithographic arrays. Letters to Nature (1992) vol. 358; p. 600.

Weigl et al., "Microfluidic Diffusion-Based Separation and Detection", Science, Jan. 15, 1999, pp. 346-347, 283-#5400, American Association for the Advancement of Science, USA.

Wolfe et al. "Dynamic Control of Liquid-Core/Liquid-Cladding Optical Waveguides." Department of Chemistry and Chemical Biology. Harvard University. Aug. 24, 2004, vol. 101, No. 34. pp. 12434-12438.

Wuite, et al., "An Integrated Laser Trap/Flow Control Video Microscope for the Study of Single Biomolecules", Biophysical Journal, Aug. 2000, vol. 29, pp. 1155-1167, Biophysical Society.

Xu et al. Dielectrophoresis of human red cells in microchips. Electrophoresis. 1999;20:1829-1831.

Zhang et al. High-speed free-flow electrophoresis on chip. Anal Chem. 2003;75:5759-5766.

"Fiber Coupled LED Source and Accessories" http://www.wt-technology.com/LED.htm, printed May 16, 2011, 1 page.

Official Action for U.S. Appl. No. 10/838,908, mailed Feb. 24, 2006.

Official Action for U.S. Appl. No. 10/838,908, mailed Oct. 30, 2006.

Official Action for U.S. Appl. No. 10/838,908, mailed Oct. 4, 2007.

Official Action for U.S. Appl. No. 10/838,908, mailed May 1, 2008, 2007.

Official Action for U.S. Appl. No. 10/838,908, mailed Mar. 4, 2009.

Notice of Allowance for U.S. Appl. No. 10/838,908, mailed Dec. 1, 2009.

Official Action for U.S. Appl. No. 11/329,491, mailed Mar. 23, 2009.

Official Action for U.S. Appl. No. 11/329,491, mailed Jun. 16, 2009.

Official Action for U.S. Appl. No. 11/329,491, mailed Jun. 3, 2010.

Official Action for U.S. Appl. No. 11/329,491, mailed Feb. 2, 2011.

Official Action for U.S. Appl. No. 11/329,491, mailed Jul. 19, 2011.

Official Action for U.S. Appl. No. 11/960,457, mailed Jun. 18, 2008.

Official Action for U.S. Appl. No. 11/960,457, mailed Jun. 25, 2008.

Official Action for U.S. Appl. No. 12/315,183, mailed Jan. 14, 2010.

Official Action for U.S. Appl. No. 12/167,136, mailed Nov. 10, 2010.

(56) References Cited

OTHER PUBLICATIONS

Official Action for U.S. Appl. No. 12/167,136, mailed May 16, 2011 8 pages.
Official Action for U.S. Appl. No. 12/203,744, mailed Mar. 29, 2011 6 pages.
Official Action for U.S. Appl. No. 12/203,744, mailed May 10, 2011 7 pages.
Official Action for U.S. Appl. No. 12/239,449, mailed Sep. 2, 2010 (Restriction Requirement).
Official Action for U.S. Appl. No. 12/239,449, mailed Jan. 5, 2011.
Official Action for U.S. Appl. No. 12/239,449, mailed May 18, 2011.
Official Action for U.S. Appl. No. 12/239,449, mailed May 1, 2014 8 pages.

* cited by examiner

OPTICAL ALIGNMENT DEFORMATION SPECTROSCOPY

CROSS REFERENCE TO RELATED APPLICATIONS

This Application claims the benefit of U.S. Provisional Application No. 61/600,482, filed Feb. 17, 2012, the entire disclosure of which is hereby incorporated herein by reference.

This invention was supported, in part, using funds provided by the terms of grants 400041, 1R01 AI079347, and/or 1R01 AI063366 awarded by the National Institutes of Health's National Institute of Allergy and Infectious Diseases. The government has certain rights to this invention.

FIELD OF THE DISCLOSURE

The disclosure relates to microfluidic systems and devices, and more specifically related to systems and devices that facilitate object deformation.

BACKGROUND

Cell mechanical properties are a broad measure of cell viability that can be quantified experimentally by measuring the cell deformability. A convenient model system for studying the interplay between cell health and cell physical characteristics is the human erythrocyte, or red blood cell (RBC). It is known that the deformability of a RBC is decreased in a number of diseases including sickle cell anemia, malaria, and diabetes.

Available techniques measure RBC deformability at either the bulk or individual cell level. Bulk testing has the advantage of being high-throughput, but provides only an averaged population deformability that can mask the presence of small populations of diseased cells. To contrast, individual cell measurements provide information on single cells, but are extremely low-throughput in nature. Currently, there is no high-throughput method to investigate the mechanical properties of populations of individual cells.

SUMMARY

Embodiments of the present disclosure have been developed to address the above-noted problems. In particular, a high-throughput single cell testing method and system for facilitating the same is described. In some embodiments, a single-cell testing method employs optical alignment compression (OAC) cytometry, where collisions between individual cells are used to induce deformation. In some embodiments, optical trapping forces within microfluidic devices are used to align cells in a non-invasive cellular manipulation on the microscale.

Microfluidics is a broad term that encompasses fluid flow in confined geometries. Typically, microfluidic devices have channels on the micrometer scale, and deal with fluid volumes on the nanoliter scale. Microfluidics provide a unique alternative to macroscale experimental techniques. The small device platform is very inexpensive to produce, and because of the decreased device volume, smaller reagent volumes are possible.

Fluid flow is characterized by the Reynolds number, a dimensionless quantity of the ratio of inertial forces to viscous forces. When the Reynolds number is much less than one, as in microfluidics, fluid flow enters the Stokes flow regime, and the effects of inertia become negligible. Small Reynolds number flows have interesting flow characteristics. The fluid flows in layers with no disturbance between the layers. Particles in Stokes flow do not quickly translate between these layers, or streamlines, without some exterior force.

Because of the wave-particle duality of light, light carries momentum. The momentum of light is defined as the ratio of Planck's constant to wavelength. Just like in classical physics, momentum of light is conserved in a closed system. As light passes through one medium into another, refraction occurs at the interface due to differing indices of refraction. The refraction is governed by Snell's Law, which states that light passing into a higher index of refraction will bend toward the normal of the interface. With the refraction, the momentum of the light changes. Since momentum is conserved, the change in momentum of the light is balanced by a change in momentum at the interface, which results in a force, dubbed the gradient force. A small percentage of light also reflects at the interface, which also induces a force, called the scattering force. When summing the forces across the full surface due to refraction and reflection, the optical trapping force can be calculated. At small length scales, forces on the order of piconewtons exerted by a diode laser can provide relevant forces, and particles like cells can be trapped by a focused laser beam.

As noted above, embodiments of the present disclosure utilize optical trapping techniques to align cells, without imparting enough force on the cells so as to induce deformation. Rather, optical trapping techniques are used to align the cells so that hydrodynamic forces cause the cells to impact one another and, therefore, experience a certain level of deformation.

In some embodiments, a microfluidic cross-flow geometry is described which flows RBCs toward each other in approximately 100 μm wide channels. As the cells are entering the junction, a linear optical trap may be used to align two incoming RBCs to allow them to enter the stagnation point in the center of the geometry. The optical trap is configured, in some embodiments, to force the cells to cross their original streamlines and cause the cells to collide at the stagnation point. The interaction between the cells is not caused by the inertia of each cell, but rather the hydrodynamic forces that are pushing the cells in flow. In some embodiments, the RBCs were swollen to avoid cell rotation in the optical trap and to make deformation analysis more uniform.

To address the need for a high throughput, non-destructive technique for measuring individual cell mechanical properties, embodiments of the present disclosure provide OAC cytometry, which combines hydrodynamic drag in an extensional flow microfluidic device with optical forces created with an inexpensive diode laser to induce measurable deformations between compressed cells. In this, a low-intensity linear optical trap aligns incoming cells with the flow stagnation point allowing hydrodynamic drag to induce deformation during cell-cell interaction. With the disclosed approach, cell mechanical properties can be measured with a throughput that improves significantly on current non-destructive individual cell testing methods.

Mechanical properties are one aspect of cell phenotype that are a marker for diseases such as cancer, diabetes, sepsis, malaria, and sickle cell anemia; for example, malaria infected RBCs are more rigid than normal RBCs. To study this link between cell stiffness and phenotype, the mechanical properties of cells have been measured indirectly in solution as well as directly on individual cells. Ektacytometers, cell filters, and rheoscopes measure properties of cell suspensions and yield average mechanical properties for cell populations; however, using these techniques it is difficult to identify small cell subpopulations such as circulating tumor cells. Micropipette aspiration, atomic force microscopy, magnetic tweezers, and single cell optical stretchers measure the properties of individual cells but are low-throughput and consequently impractical for making measurements on cell populations.

To address the need for higher throughput measurements and identifying diseased sub-populations, deformation measurements on single cells have been reported in microfluidic-based devices. Measurement rates of 1-5 cell/s in optical stretching and electroporation coupled with flow have been achieved; however, these techniques can cause cell lysis by irreversibly damaging cell membranes. To avoid this, other approaches rely on collisions of cells with solid objects placed within a flow field to induce deformation where, for example, cells forced through a series of pillars yields a throughput of 1.7 cell/s. A disadvantage of this approach is that it can be difficult to decouple cell-object interactions (i.e. lubrication forces, non-specific adhesion) from cell mechanical properties. These types of interactions can be avoided by using hydrodynamic forces in combination with inertial focusing, which has measurement rates as high as ~2,000 cells/s. While the throughput of this technique is high, the high shear rates (175,000 $s^{-1}$) and corresponding destructive shear stresses (1,750 dyn/$cm^2$) in such devices may damage biological samples and can prevent subsequent cell investigation. Such stresses are well above typical physiological values for veins and arteries (of order 1-10 dyn/$cm^2$). Furthermore, high shear stresses can induce changes in cell mechanical properties making quantification of cell properties difficult. For example, when exposed to shear stresses on the time scale of minutes, RBCs lyse at 1,500 dyn/$cm^2$, platelets become activated at 80 dyn/$cm^2$ and leukocytes lyse or experience phenotypic changes at shear stresses above 600 dyn/$cm^2$.

As disclosed herein, a cell deformation cytometry technique based on OAC where an extensional flow-field is used with a linear optical trap to force cells to meet or 'collide' at the stagnation point. Rather than using inertial or optical forces to deform cells, however, viscous stresses induced by flow around a stationary cell pair are employed to deform cells. To create a cell pair in laminar flow, forced alignment and positional control of incoming cells is leveraged. To apply the necessary forces, a linear optical trap, created using an inexpensive laser diode, is used to non-destructively and non-invasively align cells for interaction with optical powers well below intensities capable of stretching or damaging cells. Here, the linear optical trap is employed along the direction of flow to position incoming cells for contact at the device center. While the force applied to a single cell at the stagnation point is not sufficient to induce measurable deformation, the hydrodynamic forces acting on a cell pair push cells against one another and are large enough to significantly deform them, allowing for quantification of cell viscoelastic behavior using a simple constitutive model. In studies using this approach, populations of individual normal, fixed, and a mixed population of 70% normal and 30% fixed RBCs have been deformed at a rate of ~20 cells/min.

In some embodiments, only 15 µl of blood (one drop) is needed for each experiment, providing almost 100 million RBCs. The resulting deformation may be analyzed to obtain values for the change in equivalent diameter of each cell.

In accordance with at least some embodiments of the present disclosure, a microfluidic system is provided that comprises:
  a first microfluidic channel configured to carry a first fluid that contains at least a first object;
  a second microfluidic channel configured to carry a second fluid that contains at least a second object, wherein the first microfluidic channel intersects the second microfluidic channel, and wherein the intersection of the first and second microfluidic channel comprises a stagnation point; and
  an optical trap configured to align the at least a first and second object in the stagnation point so that hydrodynamic forces from the first and second fluid cause the at least a first and second object to impact one another and deform at the stagnation point.

It should be appreciated that while the term stagnation point is used herein to describe a relative point in the microfluidic system where objects from different microfluidic channels collide, a stagnation point may actually refer to an area, collection of points, or approximated point within the microfluidic system. Accordingly, the term stagnation point should not be narrowly construed to include only a point in space, but may encompass an area, a volume, a plurality of areas, a plurality of volumes, or a plurality of points.

The Summary is neither intended nor should it be construed as being representative of the full extent and scope of the present invention. The present disclosure is set forth in various levels of detail and the Summary as well as in the attached drawings and in the detailed description of the disclosure and no limitation as to the scope of the present disclosure is intended by either the inclusion or non inclusion of elements, components, etc. in the Summary. Additional aspects of the present disclosure will become more readily apparent from the detailed description, particularly when taken together with the drawings.

DETAILED DESCRIPTION

The ensuing description provides embodiments only, and is not intended to limit the scope, applicability, or configuration of the claims. Rather, the ensuing description will provide those skilled in the art with an enabling description for implementing the described embodiments. It being understood that various changes may be made in the function and arrangement of elements without departing from the spirit and scope of the appended claims.

Although embodiments of the present disclosure are generally described with systems that employ image-processing techniques to analyze object deformation, the invention is not so limited. Rather, object deformation may be analyzed by one or more of a cytometer, Coulter counter (capacitive-based, resistance-based, etc.), or the like. Furthermore, embodiments of the present disclosure contemplate that a microfluidic system may comprise a plurality of analysis cells operating in parallel, where each analysis cell comprises its own set of microfluidic channels and collision area (e.g., stagnation point).

EXAMPLE(S)

Microfluidic devices may be fabricated using standard photo and soft lithography techniques. Briefly, silicon wafer masters can be fabricated using standard photolithography using a negative photoresist. Polydimethylsiloxane (PDMS) can then be mixed in a 10:1 weight ratio of base to curing agent, poured over the wafer master, degassed, and cured in an 80° C. oven. The PDMS devices are subsequently bonded to glass cover slips using oxygen plasma.

Figure 1:
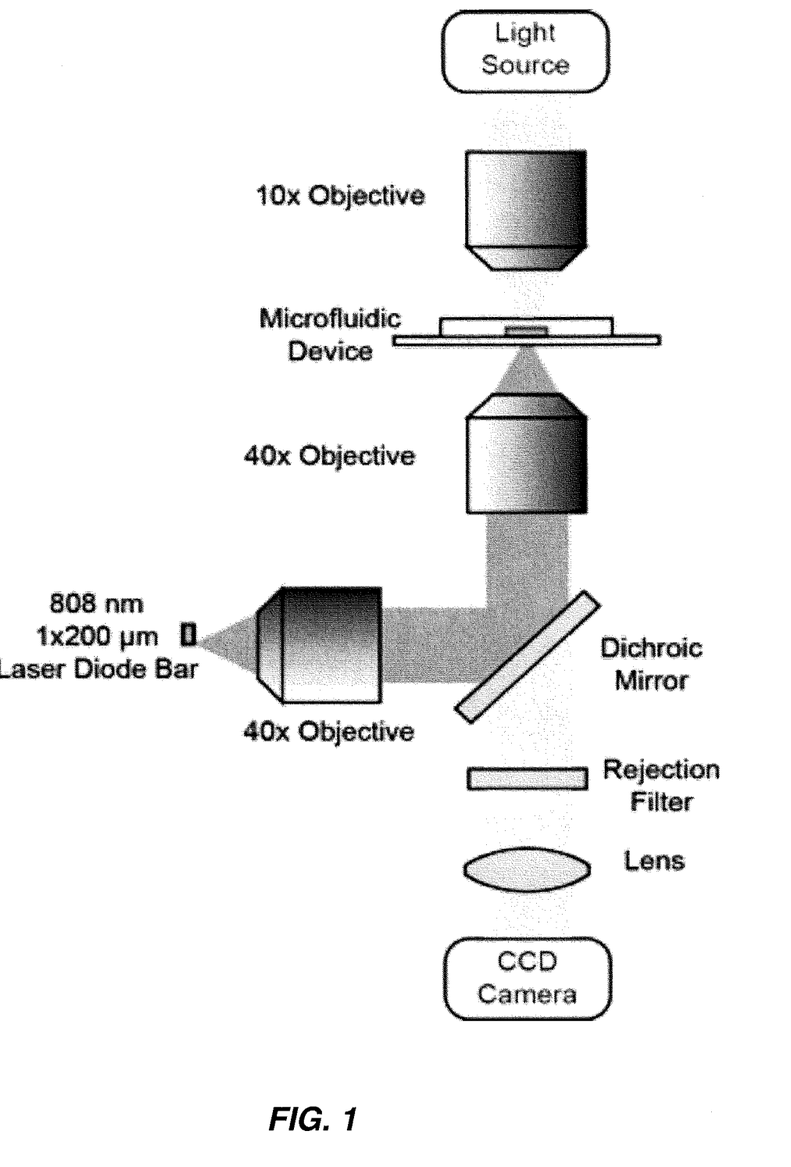
FIG. 1 is a diagram depicting an optical trapping and imaging setup in accordance with embodiments of the present disclosure.

An inverted light microscope may be used to image the cell/object interactions in the microfluidic device. White light condensed with a 10× objective illuminates the image through a 40× objective and a f=250 mm lens onto a CCD camera below the device. An identical 40× objective is used to collimate light from an 808 nm linear diode laser. The collimated laser light is reflected by a dichroic mirror into the 40× imaging objective and focused at the stagnation point of the extensional flow geometry. A rejection filter is placed between the mirror and camera to prevent the high energy laser light from damaging the camera. The wavelength and operating power of the laser were chosen to prevent damage to the cells. An example of such an optics setup is shown in FIG. 1.

Figure 2:
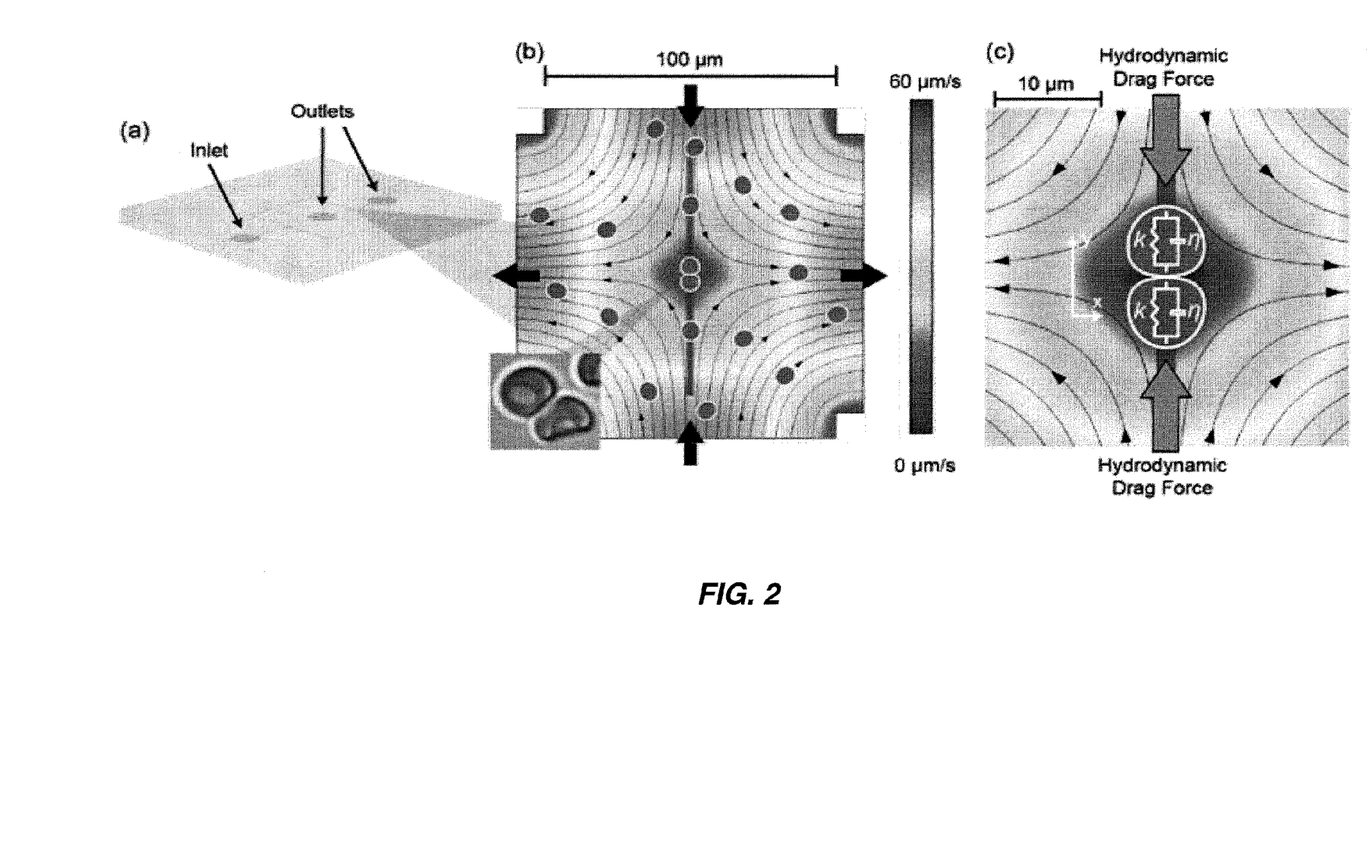
FIG. 2 depicts a microfluidic device design in accordance with embodiments of the present disclosure.
Figure 5:
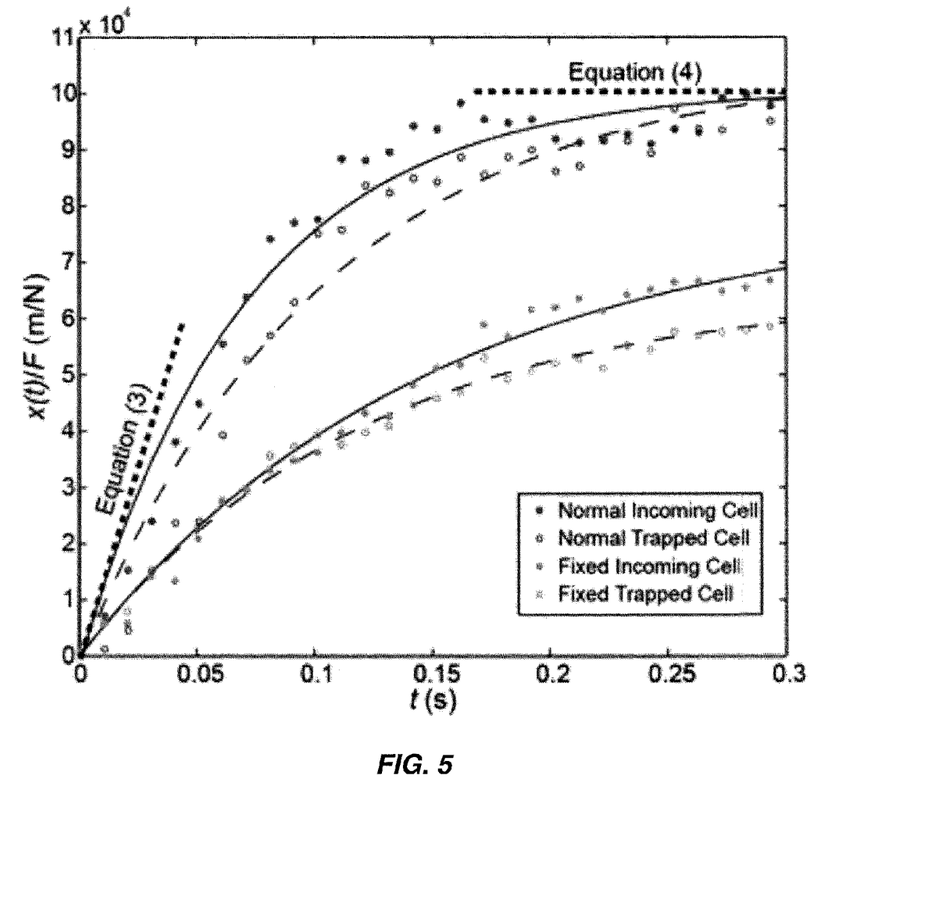
FIG. 5 is a diagram depicting experimental results from the device of FIG. 2 and the exponential fits for both cells involved in the time lapse of FIG. 3.

Extensional flow was created by bringing two axially aligned opposite flows together at a cross junction, as shown in FIG. 2. The experimental solution comprises a diluted blood sample, suspended in a solution of phosphate buffered saline (PBS), bovine serum albumin (BSA), and sodium citrate. PBS was used to control the osmolarity of the solution, inducing swelling of the cells for more simple imaging and analysis. 0.15% w/v BSA was used to prevent cell adhesion, and 1.1% w/v sodium citrate prevents coagulation. Each device was pre-soaked for one hour to prevent cell adhesion. A 13.5 µl blood sample was obtained by an anonymous donor via finger poke, and diluted to 500 µl of total solution. To compare multiple cell populations, deformation of normal RBCs were compared to glutaraldehyde-fixed RBCs. Fixed RBCs were generated by adding glutaraldehyde to the suspension described above to a final concentration of 0.01% v/v. Mixed cell populations were generated by combining PBC-washed fixed RBCs with normal RBCs in a 30:70 fixed:normal volume ratio. Results of normal and fixed cell experiments are shown in FIG. 5. Although FIG. 5 references the equivalent diameter change, one could use the major/minor axis diameter or the equivalent diameter measurement, as either works in this method.

The extensional flow geometry brings cells together at the stagnation point from opposing directions. A linear diode laser, shown in purple in FIG. 2, aligns the incoming cells, forcing them to 'collide' with each other at the center of the intersection. If not for the linear nature of the optical trap we employ, the cells would follow their corresponding streamlines and no deforming interaction would be observed. The laser power used in some embodiments, however, is not enough to perform any stretching on the cells, just enough to trap and align/guide them.

Experiments have been performed in the Stokes flow regime at a Reynolds number of $10^{-4}$, allowing inertia to be neglected. Because inertia is negligible in Stokes flow, the fluid drag on the cells causes the cells to be pushed into each other at the stagnation point. We approximate the fluid drag acting on the cells by Stokes' law, where R is the cell radius, µ is the fluid viscosity, and v is the fluid velocity.

$$F = 6\pi\mu Rv \quad (1)$$

Figure 4:
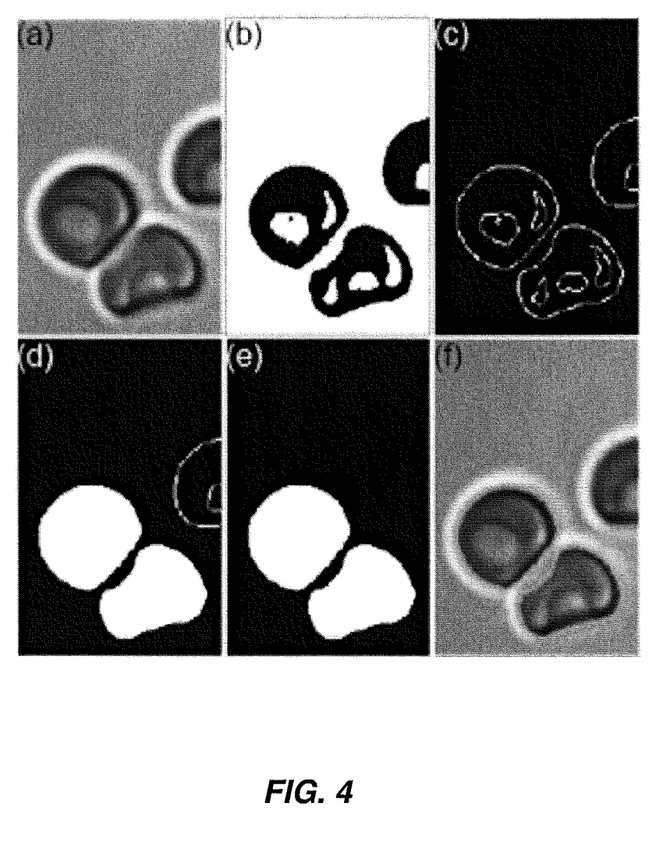
FIG. 4 is a series of images showing an image processing technique in accordance with embodiments of the present disclosure.

As the cells 'collide,' they deform until they reach a point of maximum deformation. The deformation can be quantified by measuring the profile of the cells using the image processing toolbox in any image-processing software. As shown in FIG. 4, an image processing script first read in the original video file (step (a)), then automatically thresholded each image (step (b)) in the video. The edges of the binary image were detected (step (c)), and connected components were filled (step (d)) and the small objects (approximately less than 20 µm2) were removed from processing (step (e)). In FIG. 4, the final detection is shown overlaid on the original image at step (f). Due to the anisotropic shape and varying orientation of colliding cells at 225 mOsm, departure from initial cell shape was quantified as a change in equivalent diameter, defined as the diameter of a circle with the same area as the cell. Cell velocities during each collision were measured by tracking the centroid of the incoming cell in flow at approximately one cell diameter from the stagnation point. In the rare event that the centroids were not aligned within 2 µm, corresponding to a 5% measurement error, the measurement was omitted.

After the contour of the cells was found, each cell area was computed, and the equivalent diameter of each cell was calculated by assuming a circle of identical area. As the cells deformed during 'collision,' departure from the original cell shape was quantified by the change in the equivalent diameter of the cell as a function of time. The Kelvin-Voigt (KV) model, an elastic element and viscous element in parallel (shown in FIG. 2 (c)), was used to describe the viscoelasticity of the red blood cell. The calculated drag force was related to the observed deformation to extract an elastic and viscous constant for each cell in the 'collision.'

The KV model is a simple model that allows for quantification of elastic and viscous contributions of the cell. When a force is exerted on a KV element, the force is distributed over both the elastic and viscous elements.

$$F = kx + \eta \frac{dx}{dt} \quad (2)$$

$$\frac{x(t)}{F} = \frac{1}{k}[1 - e^{-kt/\eta}] \quad (3)$$

When the differential equation in (2) is solved, a relationship between force (F) and change in equivalent diameter (x) is generated, and the elastic constant (k) and viscous constant ($\eta$) can be extracted from (3). The data generated via image processing can be seen fitted to eqn (3) in FIG. 5.

A technique is disclosed herein that employs hydrodynamic drag in conjunction with extensional flow to deform cells colliding at the stagnation point, an approach that has the potential to attain high-throughput measurement rates with less risk of cell damage.

While individual cell testing techniques such as micropipette aspiration and atomic force microscopy are capable of accurately measuring the properties of single cells, their throughputs are not adequate for collecting population data. On the other hand, high-throughput techniques such as electroporation and inertial focusing provide significantly larger data collection rates, but can damage the tested cells. The approach disclosed herein is able to non-destructively measure the mechanical properties of cells as well as generate population data. This technique also takes advantage of the geometry of the linear optical trap where it has been previously demonstrated that such anisotropic traps can sort and stretch cells at high power. In OAC, however, hydrodynamic forces, not optical forces, induce cell deformation and the optical trap is used as an alignment tool only. As a result, the optical trap intensity is an order of magnitude lower and does not contribute to cell deformation.

To quantify cell deformation, mechanical properties for each cell can be determined using measured deformation with the KV model where properties are separated into elastic and viscous contributions. Standard viscoelastic membrane behavior is shown in the limits of the KV model with the rate of membrane deformation controlled by $\eta$, and the extent of deformation controlled by k. The elasticity of a cell can be divided into three contributions: the shear modulus, the area expansion modulus, and the bending modulus. Since area dilation does not occur during OAC experiments, it can be neglected. The bending modulus in RBCs is much smaller than the elastic modulus, thereby allowing one to equate the calculated elastic constant and the elastic shear modulus. Reported values of elastic shear modulus for RBCs range from 2.5-13.5 $\mu$N/m, which is in agreement with our results for k (8.62±3.10 $\mu$N/m) by OAC. The total membrane viscosity was found to be ~1, which is comparable to the OAC results of the normal cell population (1.21±0.69 $\mu$N s/m). Population data for normal cell deformation experiments is shown in FIGS. 6, 7 and 8.

For fixed cells an increase in k can be observed (17.1±7.55 $\mu$N/m), which in agreement with previous findings. FIGS. 6, 7 and 8 show population data for fixed cell deformation experiments. Due to fixation with glutaraldehyde, the RBC membrane is stiffened, resulting in less deformation and a higher measured k. There is no significant difference, however, between $\eta$ in the two cell populations (normal: 1.21±0.69 $\mu$N s/m and fixed: 1.15±0.75 $\mu$N s/m). The viscoelastic nature of the RBC is controlled by the cytoskeleton, while the viscous contribution of the lipid bilayer and fluid cytoplasm have little effect on the deformation and relaxation response of the cell. Because of the relative contribution of k and $\eta$, it is expected that the major difference between the normal and fixed RBC populations will be found in the value of k.

Figure 6:
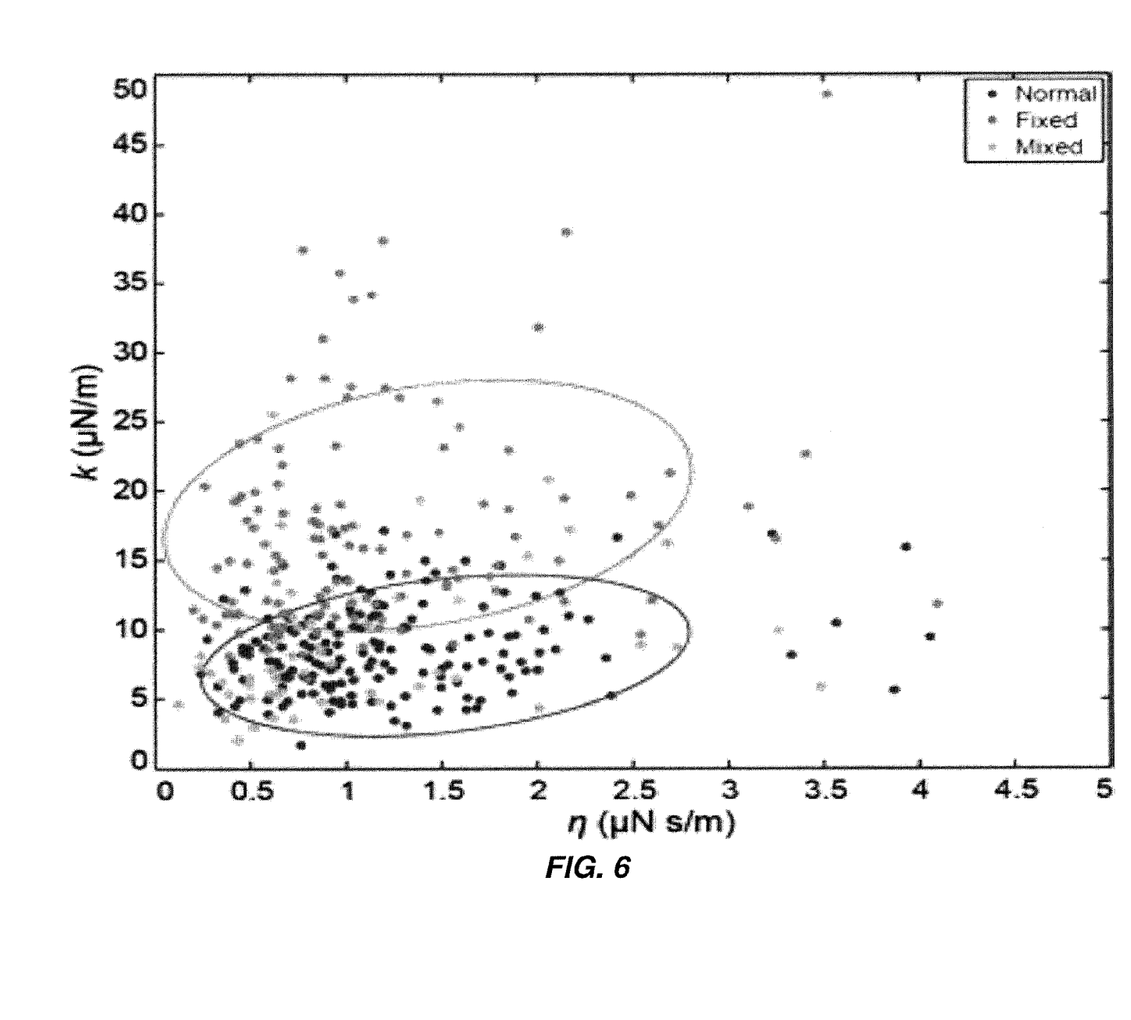
FIG. 6 depicts the mechanical property data in a cytometry style plot from population measurements performed on normal RBCs, fixed RBCs, and a mixed RBC sample.
Figure 7:
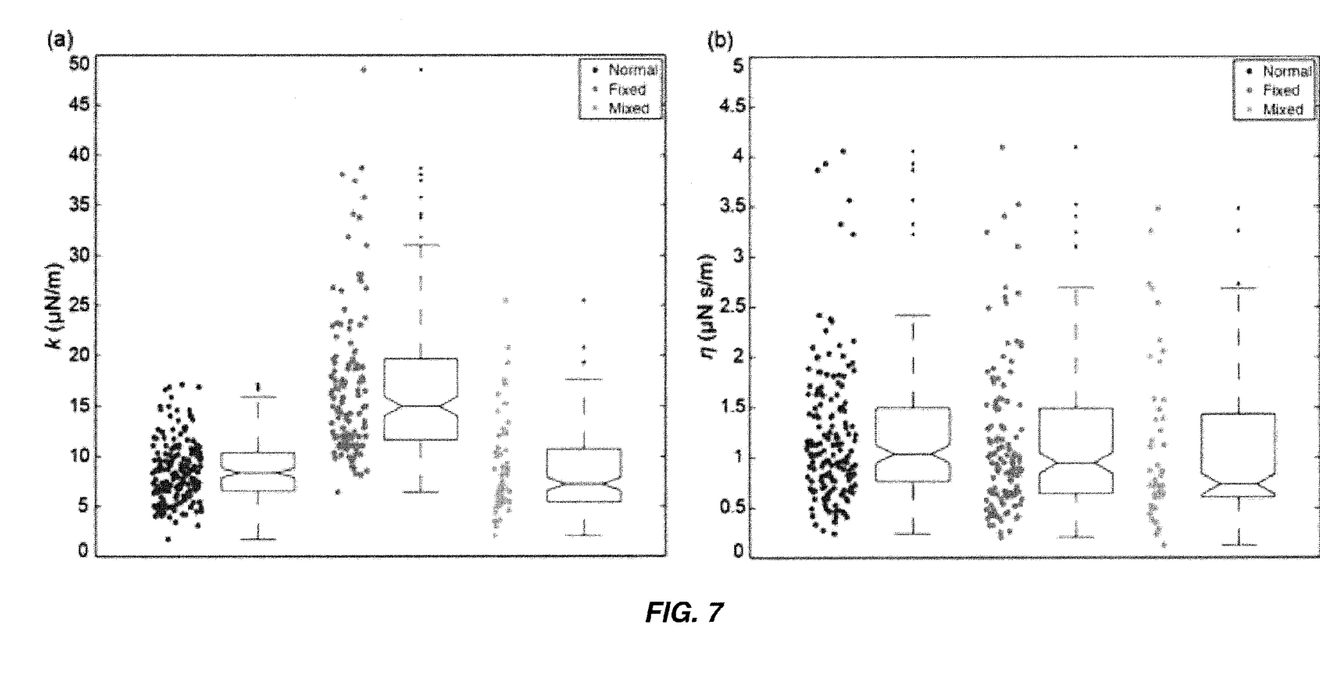
FIG. 7 depicts the elastic and viscous constants for normal, fixed, and mixed populations of cells.
Figure 8:
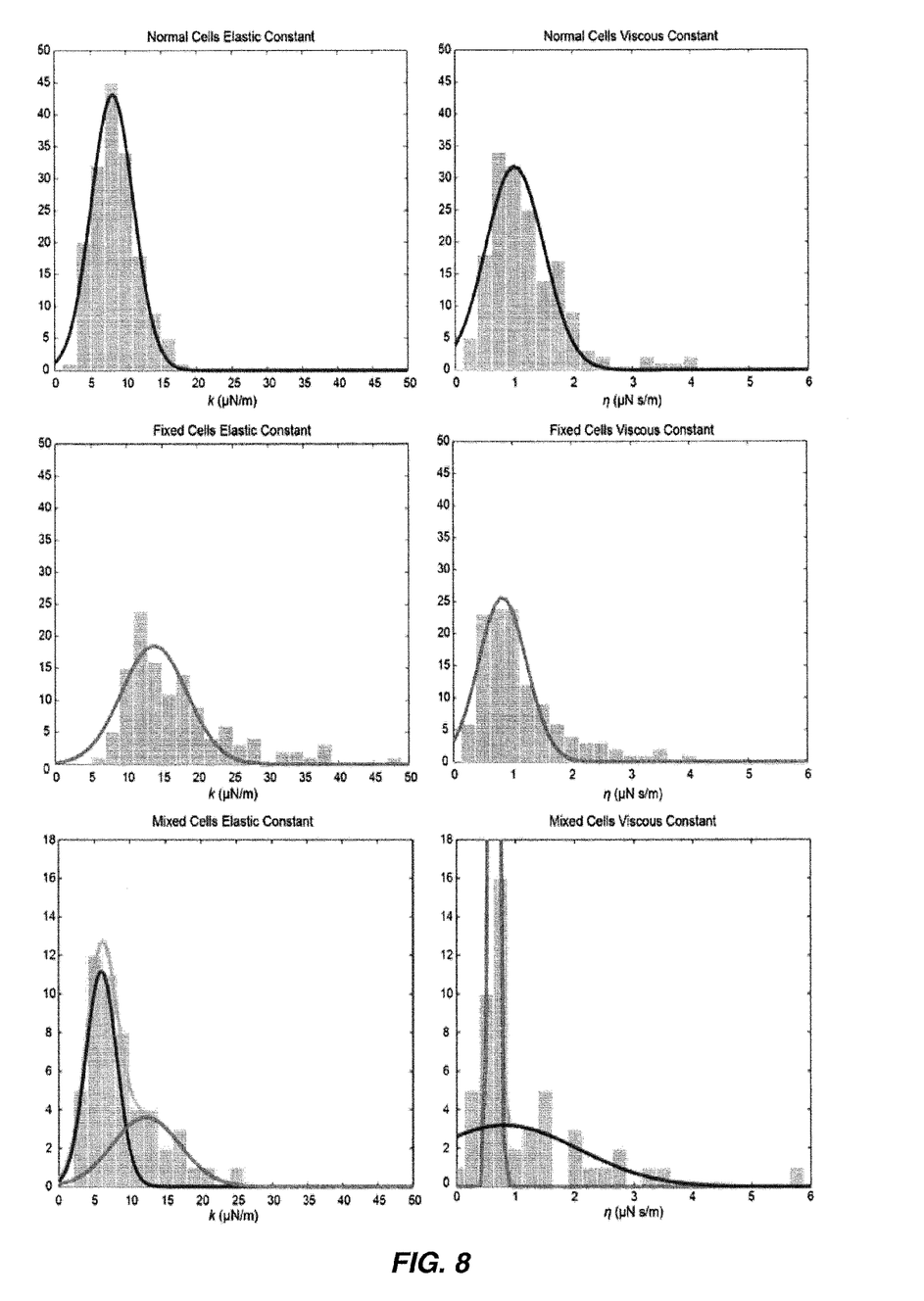
FIG. 8 depicts the Gaussian distributions for the population data in FIGS. 6 and 7.

Demonstrating such detectable differences in a mixed population without tags, in FIGS. 6, 7 and 8, a sample of 30% fixed to 70% normal cells was measured and results were compared to those determined above. In this case and fitting to two populations, it can be shown that k is approximately equal to 5.96±3.11 $\mu$N/m and 12.3±6.76 $\mu$N/m and $\eta$ is approximately equal to 0.64±0.09 $\mu$N s/m and 0.80±1.79 $\mu$N s/m with the stiffer population at 41%±9.7% of the total (Gaussian distribution fitting shown in FIG. 8). These results are indeed consistent and demonstrate the utility of OAC cytometry as a testing method, able to identify separate cell populations in a mixture without cell tagging.

Using the conditions disclosed herein, cell mechanical properties can be measured at a rate of at least ~20 cells/min and possibly as high as 100 cells/min. The theoretical throughput of OAC however is limited by the cell relaxation time ($\tau$), the time required for a cell to recover from a deformed state. In this technique, a small force is applied and cells respond by deforming at a rate set by $\tau$. Though much higher forces could be applied, the reversible approach described herein provides access to cell deformation dynamics, allowing measurement of both viscous and elastic properties. Because two cells are deformed at the same time, two measurements are simultaneously recorded, allowing for a maximum throughput of $2/\tau$. For RBCs with $\tau$=0.1 s, a throughput of 20 cells/s can be expected. While this technique does not approach the throughputs available with traditional cytometry, it instead offers a non-destructive technique for measuring the individual cell properties of small populations. Cytometry methods trade testing at lower, physiological shear rates for increases in throughput that risk damaging cells with high shear and contact forces, problems that OAC avoids. The ability to test cells in a non-invasive, non-destructive manner allows for further testing on viable cells. Studying deformation in this manner also allows for investigation into shear stress sensitive cells such as leukocytes and platelets.

Figure 3:
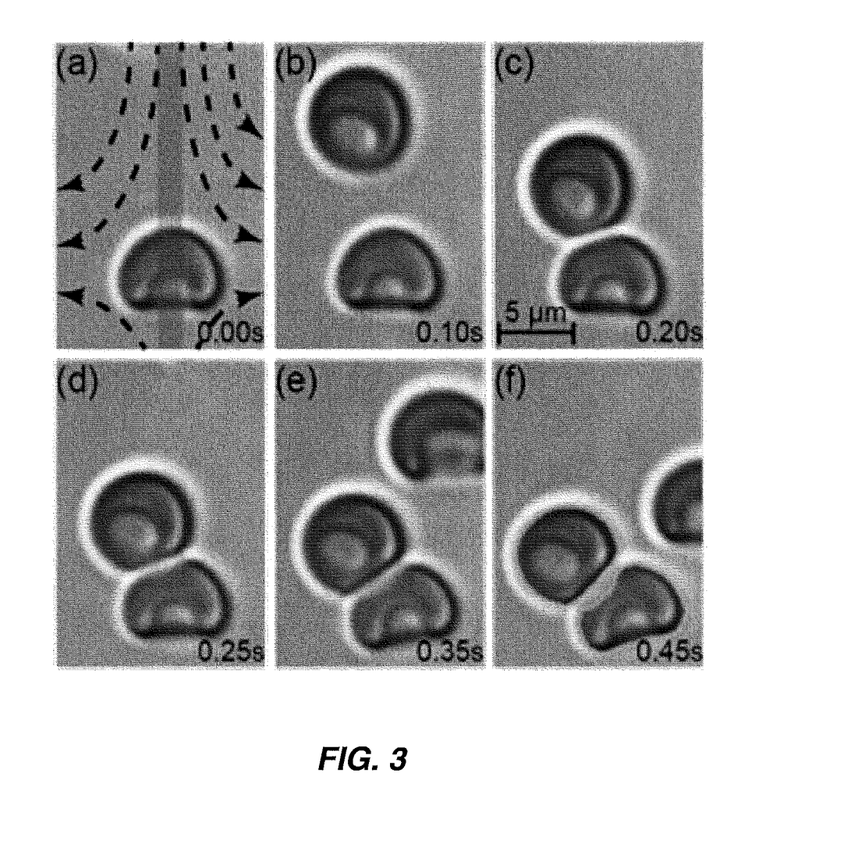
FIG. 3 is a series of images depicting cells colliding in accordance with embodiments of the present disclosure.

OAC cytometry can be used to measure deformation in non-spherical cell systems as well, as shown here with RBCs (FIG. 3). Normal RBCs exhibiting shape anisotropy will readily rotate in an optical trap; however, optical trap intensities were kept low and cells were slightly swollen to minimize rotation and observe the orientation independence of RBC properties. One could, however, readily employ slightly higher intensities that would tightly pre-orient cells for those systems that do not adopt spherical shapes, such as sickled RBCs.

FIG. 3 shows a single collision of partially swollen RBCs with a time lapse. In the first frame, the diode bar laser trap is shown in purple, and the fluid flow streamlines are shown as well. The last frame shows the contour of the processed image. FIG. 5 shows the exponential fits for both cells involved in the time lapse of FIG. 3.

As shown in FIG. 3, a typical cell collision starts with one cell held in the stagnation point by the laser trap. An incoming cell is trapped by the laser, and fluid drag pushes the cell into the trapped cell. In the first frame, streamlines are shown as dotted lines, and the optical trap is shown in light blue. It should be noted that the trap is only holding the cell in the horizontal direction, the force in the vertical direction is negligible.

Specific details were given in the description to provide a thorough understanding of the embodiments. However, it will be understood by one of ordinary skill in the art that the embodiments may be practiced without these specific details.

While illustrative embodiments of the disclosure have been described in detail herein, it is to be understood that the inventive concepts may be otherwise variously embodied and employed, and that the appended claims are intended to be construed to include such variations, except as limited by the prior art.

What is claimed is:

1. A microfluidic system, comprising:
   a first microfluidic channel configured to carry a first fluid that contains at least a first cell travelling at a first velocity;
   a second microfluidic channel configured to carry a second fluid that contains at least a second cell travelling at a second velocity, wherein the first microfluidic channel intersects the second microfluidic channel;

an optical trap configured to align the at least the first and the second cells so that hydrodynamic forces from the first and second fluid cause the at least the first and the second cells to impact one another and deform; and a reservoir comprising a phosphate buffered saline solution to induce swelling of the first and the second cells to minimize rotation.

2. The microfluidic system of claim 1, wherein at least one of the first and the second cells comprises a red blood cell.

3. The microfluidic system of claim 1, wherein the at least the first and the second cells comprise a red blood cell.

4. The microfluidic system of claim 1, further comprising:
means for analyzing a deformation of at least one of the first and the second cells while the first and second cells impact one another;
means for comparing an amount of deformation of at least one of the first and the second cells to an expected deformation of at least one of the first and second cells; and
based on the comparison, means for determining whether the at least one of the first and second cells is healthy.

5. The microfluidic system of claim 4, wherein the means for analyzing comprises an image-processor.

6. The microfluidic system of claim 4, wherein the means for analyzing comprises a Coulter counter.

7. The microfluidic system of claim 4, wherein the means for analyzing comprises a cytometer.

8. The microfluidic system of claim 1, wherein the first direction intersects with the second direction at a substantially ninety degree angle.

9. The microfluidic system of claim 1, wherein the point at which the first microfluidic channel intersects the second microfluidic channel includes at least one area or at least one volume.

10. A method, comprising:
flowing a first object in a first microfluidic channel at a first velocity;
flowing a second object in a second microfluidic channel at a second velocity;
swelling the first and the second objects to minimize rotation; and
trapping at least one of the first and the second objects with an optical trap so as to align the first object with the second object and further cause the first object to impact the second object.

11. The method of claim 10, further comprising:
analyzing a deformation of at least one of the first and the second objects;
comparing an amount of deformation of at least one of the first and the second objects to an expected deformation of at least one of the first and second objects; and
based on the comparison, determining whether the at least one of the first and the second objects is healthy.

12. The method of claim 11, wherein the analysis of the deformation is performed with image-processing techniques.

13. The method of claim 11, wherein the analysis of the deformation is performed with a Coulter counter.

14. The method of claim 11, wherein the analysis of the deformation is performed with a cytometer.

15. The method of claim 10, wherein the first microfluidic channel flows directly towards the second microfluidic channel.

16. The method of claim 10, wherein the first object and the second object correspond to a cell.

17. The method of claim 10, wherein the first microfluidic channel intersects with the second microfluidic channel at a substantially ninety degree angle.

18. The method of claim 17, wherein the point at which the first and the second microfluidic channels intersect comprises at least one area or at least one volume.

* * * * *

UNITED STATES PATENT AND TRADEMARK OFFICE
CERTIFICATE OF CORRECTION

PATENT NO. : 9,487,812 B2
APPLICATION NO. : 13/770875
DATED : November 8, 2016
INVENTOR(S) : Jeff Squier et al.

Page 1 of 1

It is certified that error appears in the above-identified patent and that said Letters Patent is hereby corrected as shown below:

In the Specification

Column 1, Line 11-15:
Delete:
"This invention was supported, in part, using funds provided by the terms of grants 400041, IR0I AI079347, and/or IROI AI063366 awarded by the National Institutes of Health's National Institute of Allergy and Infectious Diseases. The government has certain rights to this invention."

And insert:
--GOVERNMENT LICENSE RIGHTS
This invention was made with government support under grants AI079347 and AI063366 awarded by the National Institutes of Health. The government has certain rights in the invention.--

Signed and Sealed this
Twenty-eighth Day of August, 2018

Andrei Iancu
*Director of the United States Patent and Trademark Office*